(12) United States Patent
Sugimoto et al.

(10) Patent No.: US 7,452,972 B2
(45) Date of Patent: Nov. 18, 2008

(54) NUCLEIC ACIDS AND PROTEINS SHOWING INCREASED EXPRESSION DOSE UNDER SALT STRESS

(75) Inventors: Manabu Sugimoto, Kurashiki (JP); Kazuyoshi Takeda, Kurashiki (JP); Kazutoshi Ito, Nitta-gun (JP)

(73) Assignee: Sapporo Breweries Limited, Tokyo (JP)

( * ) Notice: Subject to any disclaimer, the term of this patent is extended or adjusted under 35 U.S.C. 154(b) by 0 days.

(21) Appl. No.: 11/566,443

(22) Filed: Dec. 4, 2006

(65) Prior Publication Data

US 2007/0093650 A1    Apr. 26, 2007

Related U.S. Application Data

(62) Division of application No. 10/344,369, filed as application No. PCT/JP01/06939 on Aug. 10, 2001, now Pat. No. 7,183,398.

(30) Foreign Application Priority Data

Aug. 11, 2000    (JP)    ............................. 2000-244647

(51) Int. Cl.
    *C07K 14/00*    (2006.01)
    *C07K 1/14*    (2006.01)
(52) U.S. Cl. ..................... 530/350; 435/69.1; 435/70.1; 435/71.1
(58) Field of Classification Search ....................... None
    See application file for complete search history.

(56) References Cited

U.S. PATENT DOCUMENTS 5,474,796 A    12/1995    Brennan

FOREIGN PATENT DOCUMENTS

| JP | 08-103267 | 4/1996 |
|----|-----------|--------|
| JP | 10-295380 | 11/1998 |
| JP | 11-187877 | 7/1999 |
| JP | 2000-157287 | 6/2000 |
| WO | WO 96/39020 | 12/1996 |
| WO | WO 97/13843 | 4/1997 |

OTHER PUBLICATIONS

Strong WB, Gut J, Nelson RG, Cloning and Sequence Analysis of a Highly Polymorphic *Crytosporidium parvum* Gene Encoding a 60-Kilodalton Glycoprotein and Characterization of Its 15- and 45-Kilodalton Zoite Surface ANtigen Products, Infection and Immunity, 2000, 68(7): 4117-4134.*
A. Yeo, "Molecular Biology of Salt Tolerance In the Context of Whole-Plant Physiology", Journal of Experimental botany, vol. 49, No. 323, Jun. 1998, pp. 915-929.
XP-002278689, Wing, Aug. 9, 2000.
XP-002278690, O.D. Anderson, Jul. 29, 2000.
XP-002278691, A.H. Schulman, Jan. 28, 1997.
XP-004173103, Y. Muramoto, et al., "Enhanced Expression of a Nuclease Gene in Leaves of Barley Plants Under Salt Stress", Gene, Elsevier Biomedical Press, vol. 234, No. 2, Jul. 8, 1999, pp. 315-321.
XP-001030508, I. Arrillage, et al., "Expression of the Yeast *HAL2* Gene in Tomato Increases the in Vitro Salt Tolerance of Transgenic Progenies", Plant Science, vol. 136, No. 2, Sep. 4, 1998, pp. 219-226.
XP-001007288, I. Winicov, "New Molecular Approaches to Improving Salt Tolerance in Corp Plants", Annals of Botany, vol. 82, No. 6, Dec. 1998, pp. 703-710.
D. Nelson, et al., "Salinity Tolerance-Mechanisms, Models and the Metabolic Engineering of Complex Traits", Genetic Engineering, vol. 20, 1989, pp. 153-176.
J. Sambrook, et al. "Molecular Coning: A Laboratory Manual", Expression of Cloned Genes in *E. coli*, 1989, pp. 9.46-9.62 and 11.45-11.61.
"The PCR Experimental Protocol For Plants", Shujunsha Co., Ltd., pp. 34-40, 1997.
"Experimental Protocol Without Use of Isotopes", Shujunsha Co., Ltd., vol. 1, DIG Hybridization, 1994, pp. 45-60.
"In Vitro Mutagenesis By PCR Method", Shujunsha Co., Ltd., 1995, pp. 151-158.
Shujunsha Co., Ltd., PET System Manual (Made by Novagen Inc.) or the Method Described In, "The Protein Experimental Protocol for Plants", 1998, pp. 10-21.
R. Horsch, et al., "A Simple and General Method for Transferring Genes into Plants", Science, 1985, pp. 227, 1229-1231.
J. Kyozuka, et al., "High Frequency Plant Regeneration from Rice Protoplasts by Novel Nurse Culture Methods", Mol. Gen. Genet., vol. 206, 1987, pp. 408-413.

* cited by examiner

*Primary Examiner*—Anish Gupta
*Assistant Examiner*—Julie Ha
(74) *Attorney, Agent, or Firm*—Oblon, Spivak, McClelland, Maier & Neustadt, P.C.

(57) ABSTRACT

A nucleic acid and a protein increasing expression levels under salt stress provide a nucleic acid with a nucleic acid sequence of SEQ. ID. NO. 1 in Sequence Listing, a variant nucleic acid thereof, a protein with an amino acid sequence of SEQ. ID. NO. 2 in Sequence Listing, and a variant protein thereof. Each of the nucleic acids and the proteins increases an expression level under salt stress. The nucleic acid and the protein are capable of providing a novel protein with a function to impart salt stress tolerance to a plant, and providing a novel gene encoding the novel protein.

1 Claim, 3 Drawing Sheets

SEQUENCE LISTING

```
<160> NUMBER OF SEQ ID NOS: 4

<210> SEQ ID NO 1
<211> LENGTH: 1377
<212> TYPE: DNA
<213> ORGANISM: Hordeum vulgare

<400> SEQUENCE: 1
```

-continued

```
cttttgccgg ccccgtcccc tcgcacacaa ggaagcatag aaggagaagc agctgctgct    60
gtaatggaac aaaatccatg gaagtttcac agcatcgtac gctatgtgtt gctttgtgtg   120
gcgagcattc atgaggcgat gcggtctatg tggtctcgca gagacgccat ccactccgac   180
aagcccatat atcatctccc cactgtgatg cttgttcgag ctgatgggtc aatcaataac   240
aacactcgta taaaggattc ttttgaagtt cgattcccca tgacaaccgc aacaaaggga   300
gactttgata caagatcgg ctcccatacg atgcatgaac gggagatttt cagtgcacgt   360
caccaactct tctacgtgat gttttttgct ggccatctga ttgatcaaac acttgcctgc   420
ctaaaatcta cgctgcaaac aagcatcctg aaaaggaaac ggaggtcgcg ctccgtatca   480
cgcacggata gaatcgctcg agaaactcca gcgggaagta ctggcggtct gtatcacgat   540
ggaatgggtg acgttgacac ccttccagcg gcatctctac acgtacagaa caaactgaac   600
atagtttctc gcaagaatgg ttttgaatac tatacaggag gcttggagga tgtagatgta   660
attcgggaac atcaaagcat catagaggaa gcggagagga aaaccgcaac aacctgggtg   720
gtcgccaccg cagctacaca gcacgcgacg gggaaccgtg acctcctatc cggtttaacg   780
cccgatcaac cgggccgctt cgttctctcg gccgacggag cggcgcccat gcaggtcgtc   840
gcccacggct gtgtcatcac aaacacggtg gttctcccca acgtgctgta cgtcccaggg   900
ctcacggcta acctcgtctc tgccagtcag cttgtcgagc tcaactacac cctcgagttt   960
agccgtggtg cgtgtcatat caggagtgcc gccgaggcac catcgtcggc aaagccagtg  1020
ttgttggaga agtggttttg ttcgagttgg acttcctgaa agtcctgcct tcaataaaca  1080
tgcgcgttct ttgaaacata aaagcgagga gatctaatta ttcctcttac ctatgcatgt  1140
ttgagtatag aaactcatgg tggcatgtaa tttgaataag tgcatgggcc tgcagctgat  1200
tagtatggcc aaatgcagct tcgtattggg cgtgtatgcc ctaacaaact aagaaaccat  1260
gtttggtcaa tttgatatac atgtatcccc tcgaaaaaat attaaatagt catgtatgta  1320
gtatatgttg gaaatatgcc cgaaaggcaa taataaatag ttattattat tgtttcg     1377
```

<210> SEQ ID NO 2
<211> LENGTH: 331
<212> TYPE: PRT
<213> ORGANISM: Hordeum vulgare

<400> SEQUENCE: 2

```
Met Glu Gln Asn Pro Trp Lys Phe His Ser Ile Val Arg Tyr Val Leu
1               5                   10                  15

Leu Cys Val Ala Ser Ile His Glu Ala Met Arg Ser Met Trp Ser Arg
                20                  25                  30

Arg Asp Ala Ile His Ser Asp Lys Pro Ile Tyr His Leu Pro Thr Val
            35                  40                  45

Met Leu Val Arg Ala Asp Gly Ser Ile Asn Asn Asn Thr Arg Ile Lys
        50                  55                  60

Asp Ser Phe Glu Val Arg Phe Pro Met Thr Thr Ala Thr Lys Gly Asp
65                  70                  75                  80

Phe Asp Asn Lys Ile Gly Ser His Thr Met His Glu Arg Glu Ile Phe
                85                  90                  95

Ser Ala Arg His Gln Leu Phe Tyr Val Met Phe Phe Ala Gly His Leu
            100                 105                 110

Ile Asp Gln Thr Leu Ala Cys Leu Lys Ser Thr Leu Gln Thr Ser Ile
        115                 120                 125

Leu Lys Arg Lys Arg Arg Ser Arg Ser Val Ser Arg Thr Asp Arg Ile
```

```
               130                 135                 140
Ala Arg Glu Thr Pro Ala Gly Ser Thr Gly Leu Tyr His Asp Gly
145                 150                 155                 160

Met Gly Asp Val Asp Thr Leu Pro Ala Ala Ser Leu His Val Gln Asn
                165                 170                 175

Lys Leu Asn Ile Val Ser Arg Lys Asn Gly Phe Glu Tyr Tyr Thr Gly
                180                 185                 190

Gly Leu Glu Asp Val Asp Val Ile Arg Glu His Gln Ser Ile Ile Glu
                195                 200                 205

Glu Ala Glu Arg Lys Thr Ala Thr Thr Trp Val Val Ala Thr Ala Ala
210                 215                 220

Thr Gln His Ala Thr Gly Asn Arg Asp Leu Leu Ser Gly Leu Thr Pro
225                 230                 235                 240

Asp Gln Pro Gly Arg Phe Val Leu Ser Ala Asp Gly Ala Ala Pro Met
                245                 250                 255

Gln Val Val Ala His Gly Cys Val Ile Thr Asn Thr Val Val Leu Pro
                260                 265                 270

Asn Val Leu Tyr Val Pro Gly Leu Thr Ala Asn Leu Val Ser Ala Ser
                275                 280                 285

Gln Leu Val Glu Leu Asn Tyr Thr Leu Glu Phe Ser Arg Gly Ala Cys
                290                 295                 300

His Ile Arg Ser Ala Ala Glu Ala Pro Ser Ser Ala Lys Pro Val Leu
305                 310                 315                 320

Leu Glu Lys Val Val Cys Ser Ser Trp Thr Ser
                325                 330

<210> SEQ ID NO 3
<211> LENGTH: 27
<212> TYPE: DNA
<213> ORGANISM: Artificial Sequence
<220> FEATURE:
<223> OTHER INFORMATION: Synthetic DNA

<400> SEQUENCE: 3
gcagctgctg ctcatatgga acaaaat                                        27

<210> SEQ ID NO 4
<211> LENGTH: 27
<212> TYPE: DNA
<213> ORGANISM: Artificial Sequence
<220> FEATURE:
<223> OTHER INFORMATION: Synthetic DNA

<400> SEQUENCE: 4
ttgaaggcag gatcctcagg aagtcca                                        27
```

NUCLEIC ACIDS AND PROTEINS SHOWING INCREASED EXPRESSION DOSE UNDER SALT STRESS

This application is a Divisional of U.S. application Ser. No. 10/344,369, filed on Jul. 30, 2003, now allowed, which is the national stage of PCT/JP01/06939, filed Aug. 10, 2001.

TECHNICAL FIELD

The present invention relates to a novel protein which increases an expression level under salt stress and to a novel gene encoding the protein.

BACKGROUND ART

Most of the soil in dry regions or coastal areas on earth contains salts and therefore is not deemed favorable for vegetation. There are problems that crops cannot grow in such lands, or cannot reap sufficient harvests even if the crops can grow there. However, development of crops which can grow in such lands has been eagerly expected to deal with expansion of dry regions attributable to global warming and to deal with population increases in developing countries. Accordingly, there is an urgent need to develop salt-tolerant crops by means of breeding or genetic engineering.

Meanwhile, most of plants growing on earth are exposed to various environmental stresses such as high temperature, low temperature, dry weather, and high salinity. The plants continue to grow by exerting resistance to those stresses in some way. To be more precise, it is known that various stress response genes operate when a plant is exposed to the foregoing environmental stresses, and the plant shows resistance to the environmental stresses by performing physiological responses at the cellular level. The genes considered to cause the plant to exert such a function have been already isolated by a subtraction hybridization method and by a differential screening method.

However, it is considered that there are enormous numbers of genes responsive to environmental stresses as the plants show various inductions of gene expressions and inhibition patterns depending on differences in environmental stress factors and in plant species. Accordingly, the present situation is still far to isolation of all the relevant genes, and isolation of these genes is now in the process of energetic efforts.

Meanwhile, there are two methods to produce or breed a salt stress tolerant plant, namely, a method of producing a salt stress tolerant transgenic plant by artificially introducing a gene related to salt stress tolerance into a plant cell, and a method of introducing the gene taken from a salt stress tolerant plant into a plant targeted for breeding by use of crossing technologies. In order to realize these, it is necessary to isolate the gene(s) related to salt stress tolerance and clarify functions thereof.

Some genes which are subjected to induction of expression under salt stress have been known to exist to date (Yao, A., Molecular biology of salt tolerance in the context of whole-plant physiology, J. Exp. Bot., 49, 915-929 (1998), Nelson, D. E., Shen, B., and Bohnert, H. J. Salinity tolerance-mechanisms, models and the metabolic engineering of complex traits, Genetic Engineering, 20, 153-176 (1998)). However, in order to develop a plant having higher tolerance, it is considered to be important to isolate more genes related to salt stress tolerance to progress in functional analyses thereof.

DISCLOSURE OF THE INVENTION

The present invention has been made in consideration of the above-mentioned problem of the prior art. It is an object of the present invention to provide a novel protein which increases an expression level under salt stress and has a function to equip a plant with salt stress tolerance, and to provide a novel gene encoding the protein.

As a result of extensive researches for attaining the object, the inventors of the present invention have found out a Sub4 gene, which is the novel gene that increases an expression level under salt stress, and thus have consummated the present invention.

Specifically, a nucleic acid of the present invention to be subjected to the induction of the expression under salt stress is a nucleic acid including a nucleic acid sequence of SEQ. ID. NO. 1 in Sequence Listing.

Moreover, another nucleic acid of the present invention to be subjected to the induction of the expression under salt stress is a nucleic acid including part of a nucleic acid sequence of SEQ. ID. NO. 1 in Sequence Listing.

Here, yet another nucleic acid of the present invention to be subjected to induction of the expression under salt stress may be a nucleic acid which hybridizes under a stringent condition with any one of the foregoing nucleic acids or with a nucleic acid having a complementary nucleic acid sequence to any one of the foregoing nucleic acids.

Moreover, still another nucleic acid of the present invention to be subjected to induction of the expression under salt stress is a nucleic acid including a nucleic acid sequence encoding an amino acid sequence of SEQ. ID. NO. 2 in Sequence Listing.

Meanwhile, a protein of the present invention to be subjected to induction of the expression under salt stress is a protein including the amino acid sequence of SEQ. ID. NO. 2 in Sequence Listing.

Here, the protein of the present invention to be subjected to induction of the expression under salt stress may include an amino acid sequence, which has any of substitution, deletion, insertion and addition of at least one amino acid in the amino acid sequence of SEQ. ID. NO. 2 in Sequence Listing, and which increases an expression level under salt stress.

BEST MODES FOR CARRYING OUT THE INVENTION

Figure 1:
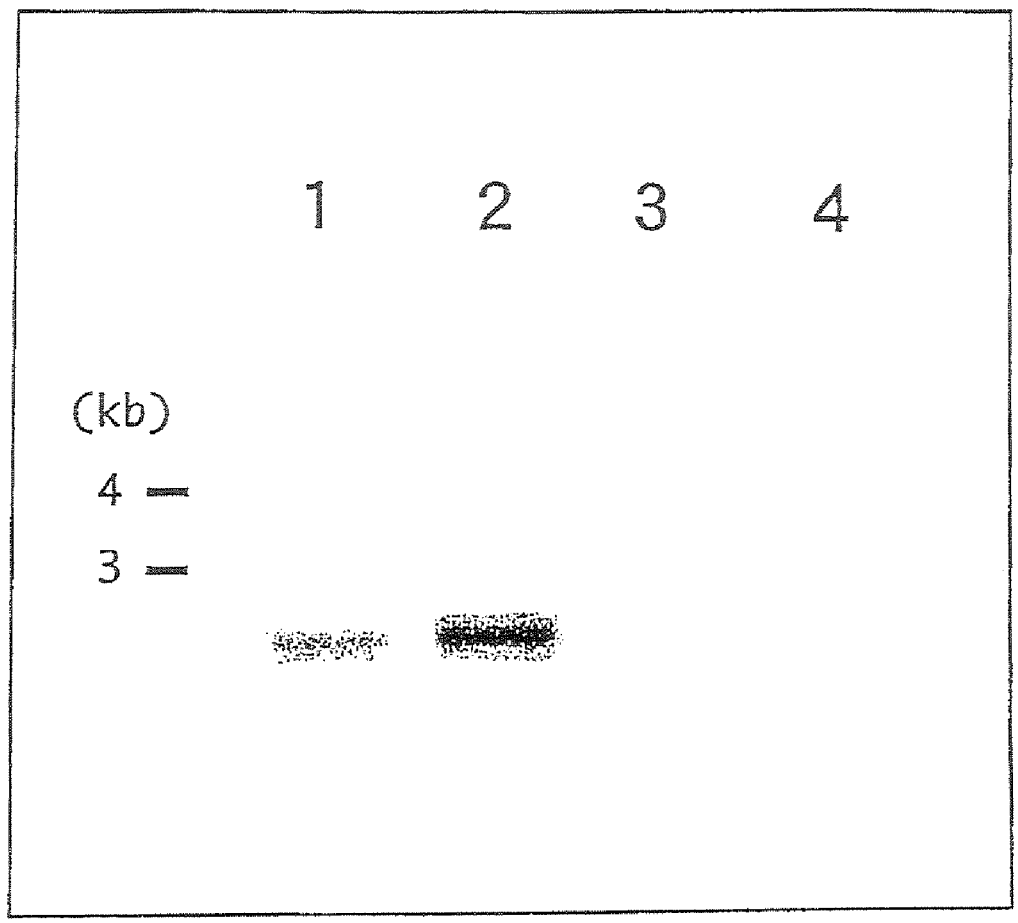
FIG. 1 is an electrophoretic photograph showing a result of identifying a gene showing expression specifically in salt stress tolerant barley by use of the Northern analysis.

Now, a preferred embodiment of the present invention will be described in detail.

A "nucleic acid" in the present invention means a deoxyribonucleic acid (DNA), a ribonucleic acid (RNA), or a polynucleotide which can be an active DNA or RNA being subjected to induction. Preferably, the nucleic acid is the DNA and/or the RNA.

Moreover, "to hybridize under a stringent condition" in the present invention means mutual hybridization of two nucleic acid fragments under a hybridization condition as described in Sambrook, J. et al, "Expression of cloned genes in E. coli" (Molecular Cloning: A laboratory manual (1989)) Cold Spring Harbor Laboratory Press, New York, USA, 9.47-9.62 and 11.45-11.61.

To be more precise, the "stringent condition" means performing hybridization in 6.0×SSC at about 45° C. and then washing in 2.0×SSC at 50° C. In order to select stringency, the salt concentration in the washing process can be selected in a range from about 2.0×SSC at 50° C. as low stringency to about 0.2×SSC at 50° C. as high stringency. Moreover, the temperature in the washing process can be elevated from the room temperature at about 22° C. of the low stringency condition up to about 65° C. of the high stringency condition.

Firstly, description will be made regarding a nucleic acid of the present invention.

The nucleic acid of the present invention is found in and isolated from a root of a variety of barley having highly tolerant to salt stress, and is characterized by increasing an expression level or exhibiting expression specifically under salt stress. The nucleic acid includes a nucleic acid sequence of SEQ. ID. NO. 1 in Sequence Listinging, which has 1377 bases. Here, the "isolated" state means a nucleic acid or polypeptide, which does not virtually contain a cell material and a culture medium when the nucleic acid or the polypeptide is formed by the DNA recombination technology or does not virtually contain a precursor chemical substance or other chemical substances when the nucleic acid or the polypeptide is chemically synthesized.

In this specification, the condition "under the salt stress" means an unfavorable condition for vegetation attributable to an elevation in the sodium chloride concentration of the soil in the nature. In a laboratory, the condition "under the salt stress" means a condition that the culture fluid for growing a plant contains the sodium chloride concentration of which is higher than a sodium chloride concentration contained in a normal culture fluid. For example, the condition under the salt stress is preferably a condition containing 1 wt % to 20 wt % of sodium chloride, or more preferably a condition containing 1 wt % to 10 wt % of sodium chloride.

Moreover, in this specification, the description "increasing an expression level under the salt stress" means an increase in an expression level of a protein or a gene observed when the protein or the gene is shifted from a normal salt concentration to exposure under the above-described salt stress. In this case, such an increase also includes the aspect that the protein or the gene does not show expression at all under the normal salt concentration but shows expression specifically under the salt stress. Here, the degree of the increase in the expression level of the protein or the gene is not particularly limited.

Meanwhile, the nucleic acid of the present invention may be a nucleic acid including part of the nucleic acid sequence of SEQ. ID. NO. 1 in Sequence Listing. Here, the description "including part of the nucleic acid sequence of SEQ. ID. NO. 1 in Sequence Listing" does not particularly limit the number of bases therein so far as the nucleic acid includes part of the nucleic acid sequence of SEQ. ID. NO. 1 in Sequence Listing.

Furthermore, the nucleic acid of the present invention may be characterized by including a nucleic acid sequence which hybridizes under the stringent condition with any one of the nucleic acids including the nucleic acid sequence of SEQ. ID. NO. 1 in Sequence Listing, the nucleic acid including part of the above-described nucleic acid sequence, and a nucleic acid having a complementary nucleic acid sequence. In this case, the nucleic acid sequence of the nucleic acid is not particularly limited so far as the nucleic acid satisfies the above-described condition. To be more precise, for example, in the nucleic acid, the bases which collectively constitute the nucleic acid sequence of SEQ. ID. NO. 1 in Sequence Listing may include one or more bases of deletion, substitution, insertion, addition or the like. Here, the above-mentioned "deletion, substitution, insertion, and addition" may include not only deletion, substitution, insertion, and addition involving a short sequence of 1 to 10 bases, but also include deletion, substitution, insertion, and addition involving a long sequence of 10 to 100 bases.

In addition, another nucleic acid of the present invention is characterized by including a nucleic acid sequence encoding an amino acid of SEQ. ID. NO. 2 in Sequence Listing. The nucleic acid sequence is not particularly limited so far as the nucleic acid encodes for the amino acid.

Next, description will be made regarding a protein of the present invention.

The protein of the present invention is characterized by including the amino acid sequence of SEQ. ID. NO. 2 in Sequence Listing. The protein has 331 of amino acids. Here, the protein of the present invention may be a protein, which includes an amino acid sequence having any of substitution, deletion, insertion and addition of one or more amino acids in the amino acid sequence of SEQ. ID. NO. 2 in Sequence Listing, and which increases an expression level under the salt stress.

Specifically, there are some proteins including amino acid sequences having substitution or deletion of one or more amino acids in the amino acid sequence of SEQ. ID. NO. 2 in Sequence Listing, and some proteins including amino acid sequences having insertion or addition of one or more amino acids in the amino acid sequence of SEQ. ID. NO. 2 in Sequence Listing, each of which increases a expression level under the salt stress. All these proteins are deemed to be mutant proteins of the protein of the present invention of SEQ. ID. NO. 2 in Sequence Listing, and are included in the protein of the present invention so far as these proteins have the characteristic of increasing an expression level under the salt stress.

Moreover, sugar chains are added to many proteins and such addition of sugar chains can be controlled by converting one or more amino acids therein. In respect of the amino acid sequence of SEQ. ID. NO. 2 in Sequence Listing, a protein subjected to control of addition of a sugar chain thereto shall be also included in the protein of the present invention so far as such a protein has a characteristic of increasing an expression level under the salt stress.

Next, description will be made regarding a preferred method of isolating a novel gene according to the present invention.

The novel gene according to the present invention can be isolated by the following Steps (1) to (7), and the isolated gene can be confirmed to exert the salt stress tolerance in the subsequent Step (8).

(1) Isolation of a cDNA Fragment which Increases an Expression Level Under the Salt Stress In order to isolate a cDNA fragment which increases a expression level under the salt stress, an adaptable mode is comparing expression levels of genes between a variety of an object plant considered to have relatively high tolerance to the salt stress (such as barley K305) and a variety of the object plant considered to have relatively low tolerance to the salt stress (such as barley I743) and thereby isolating the gene found to be increasing the expression level specifically or strongly out of the variety considered to have relatively high tolerance to the salt stress. Moreover, it is also possible to isolate the gene which increases the expression level by means of exposing the above-mentioned plants under the salt stress at a higher salt concentration. To be more precise, for example, a plant seed may be grown for 12 hours after germination by adding 50 to 1000 mM of sodium chloride to a culture fluid, and then roots thereof may be collected and used as a sample.

Next, total RNA and mRNA are prepared out of the sample thus produced. Preparation of the total RNA out of a plant tissue (such as the root, a leaf, or a stem) of the plant targeted for gene isolation may be carried out by publicly-known methods including the method described in "The PCR experimental protocol for plants, p. 56, 1999, Shujunsha Co., Ltd.", for example. It is also possible to use publicly-known methods of preparing mRNA out of the total RNA thus obtained. Such preparation can be carried out in accordance with the protocol attached to "Dynabeads Oligo $(dT)_{25}$" (made by Veritas Corp.), for example.

By using the total RNA or the mRNA thus obtained, isolation of the targeted gene can be carried out in accordance with a subtraction hybridization method or a differential screening method, for example. The subtraction hybridization method and the differential screening method may be carried out by use of publicly-known methods. For example, such methods may be carried out in accordance with the protocol attached to "PCR Select cDNA Subtraction Kit" (made by Clontech).

(2) Northern Hybridization Analysis (Hereinafter Referred to as the "Northern Analysis")

The Northern analysis using the isolated salt stress tolerant barley-specific gene as a probe can be performed in order to confirm as to whether the isolated salt stress tolerant barley-specific gene actually increases the expression level or manifests specifically in the salt stress tolerant barley. The Northern analysis can be carried out by publicly-known methods, for example, based on the method described in "Experimental protocol without use of isotopes, Vol. 1, DIG Hybridization, p. 45, 1994, Shujunsha Co., Ltd." and the like.

(3) Fabrication of a cDNA Library Specifically Emerging in the Salt Stress Tolerant Plant Under the Salt Stress.

A cDNA library can be fabricated by publicly-known methods from the mRNA prepared in Step (1). Such fabrication of the cDNA can be carried out in accordance with the protocol attached to "Marathon cDNA Amplification Kit" (made by Clontech), for example.

(4) Isolation of a Salt Stress Tolerant Plant-Specific cDNA

Isolation of a salt stress tolerant plant-specific cDNA can be performed by screening the cDNA library, which is fabricated by use of the salt stress tolerant plant as described above, by using a salt stress tolerant plant-specific probe. Such screening can be performed by publicly-known methods. For example, the method described in the protocol attached to "AlkPhos Direct system for chemiluminescence" (made by Amersham Pharmacia Biotech) may be used.

Meanwhile, as for labeling the salt stress tolerant plant-specific cDNA fragment used as the probe, radioisotopes such as $^{32}P$, $^{33}P$ or $^{35}S$, fluorescent labeling agents, and the like may be used. For example, such labeling may be carried out by use of the method described in the protocol attached to "AlkPhos Direct system for chemiluminescence".

(5) Base Sequence Determination and Homology Search

The base sequence of the isolated gene can be determined by publicly-known methods. For example, such determination can be performed in accordance with the protocol attached to "BigDye Terminator Cycle Sequencing FS Ready Reaction Kit" (made by Perkin Elmer Inc.), for example. Based on the base sequence determined here, it is possible to check for presence and level of homology with any other known genes obtained from other plant species by means of performing homology search regarding the obtained based sequence by use of a database (such as http://www.ncbi.nlm.nih.gov/BLAST/). In this way, it is possible to judge as to whether the obtained gene is a novel gene or not.

(6) Isolation of an Open Leading Frame of the Salt Stress Tolerant Plant-Specific cDNA In order to isolate only an open leading frame out of the above-described cDNA, amplification by the PCR method may be performed by use of the cDNA as a template while applying an oligonucleotide primer containing a start codon (ATG) and an oligonucleotide primer containing a stop codon. In this event, introduction to the after-mentioned expression vector is facilitated by performing PCR using the oligonucleotide primers, which are arranged by introducing proper recognition sites for restriction enzymes to the 5' ends of the two oligonucleotide primers mentioned above. Here, the "open leading frame" means the most distant region from the start codon (ATG) to the stop codon (TGA, TAG or TAA) within the nucleic acid sequence of the cDNA. Isolation of the above-described open leading frame can be performed by the method described in "The PCR experimental protocol for plants, p. 69, 1995, Shujunsha Co., Ltd.", for example.

(7) Expression of the Open Leading Frame of the Salt Stress Tolerant Plant-Specific cDNA A plasmid is assembled by introducing the open leading frame region of the salt stress tolerant plant-specific cDNA isolated in Step (6) to an *Escherichia coli* expression vector (the pET System such as pET15b). Thereafter, the plasmid is introduced to an *Escherichia coli* (such as *E. coli* BL21(DE3) pLysS), and then IPTG is added to a culture fluid for the transformed *Escherichia coli* strain. In this way, an induction of expression of a protein encoded in the open leading frame becomes feasible. The above-described induction of expression can be performed by publicly-known methods, such as the method described in "pET System Manual" (made by Novagen Inc.) or the method described in "The PCR experimental protocol for plants, p. 9, 1998, Shujunsha Co., Ltd.".

(8) Measurement of Salt Stress Tolerance of the Transformed *Escherichia coli*

As shown in Step (7), the transformed *Escherichia coli*, in which a gene product considered to be related to the salt stress tolerance is subjected to the induction of expression, is cultivated in a culture medium containing the sodium chloride which concentration is 1 wt % to 10 wt %, for example, and a growth rate thereof is measured. In this way, it is possible to confirm as to whether or not the gene is related to the salt stress tolerance.

Next, description will be made regarding fabrication of a transgenic plant made by introducing the gene obtained through the foregoing steps.

The gene obtained through the foregoing steps is considered to have the effect, which is to provide a plant having the gene with salt stress tolerance by an increase in expression under the salt stress. Therefore, development of a plant having salt stress tolerance is feasible if the above-described gene can be introduced to a plant which originally does not have the salt stress tolerance by use of a genetic engineering method.

As for a method of fabricating such a transgenic plant, the gene obtained in the foregoing steps may be firstly inserted into a cloning vector for a plant cell, and the obtained plasmid may be introduced to a plant targeted for the salt stress tolerance. The cloning vector usable herein includes, for example, binary vector plasmids such as pBI2113, pBI101, pBI121, pGA482, pGAH and pBIG, and intermediate vector plasmids such as pLGV23Neo, pNCAT and pMON200. When a binary vector plasmid is used, the targeted gene may be inserted between boundary sequences (LB and RB) of the binary vector and then introduced into an *Escherichia coli* for amplification. Thereafter, the plasmid may be purified and introduced into a bacterium that belongs to the *Agrobacterium* genus (such as a strain of *Agrobacterium tumefaciens* EHA101) for use in transduction of the plant. As for the method of introducing the plasmid to the bacterium, the freeze-thawing method, the electroporation method, and the like are preferably applied.

Transformation of the plant is feasible by infecting the plant with the transformed *Agrobacterium* thus obtained. The leaf disk method, the protoplast method, and the like may be applied as the method of transformation (Horsch, R. B., Fry, J. E., Hoffmann, N. L., Eichholtz, D., Rogers, S. G., and Fraley, R. T. "A simple and general method for transferring into plants", Science 227, 1229-1231 (1985), Kyozuka, J., Hayashi, Y., and Shimamot, K., "High frequency plant regeneration from rice protoplasts by novel nurse culture methods", Mol. Gen. Genet. 206, 408-413 (1987)).

Alternatively, it is also possible to apply a method of directly introducing the targeted gene to the plant without using the *Agrobacterium*. To be more precise, such a method includes the particle gun method, the polyethylene glycol method, the liposome method, and the micro-injection method, for example.

Moreover, a host plant for introduction of the gene includes not only crops such as barley, rice, corn, tobacco, *Arabidopsis*, wheat, soybean, and tomato, but also cultured cells, plant organs (for example, root, leaf, petal, rhizome, seed and the like) and plant tissues (for example, epidermis, phloem, parenchyma, xylem, vascular strand and the like) thereof.

Fabrication of a transgenic plant having salt stress tolerance is feasible by introducing the nucleic acid of the present invention to the host plant as described above.

EXAMPLES

Now, the present invention will be described in more detail based on examples. However, it is to be understood that the present invention shall not be particularly limited to the examples described below.

Example 1

(Preparation of a Root of Salt Stress Tolerant Barley and a Root of Salt Stress Sensitive Barley)

A seed of barley K305, which is a variety of salt stress tolerant barley, and a seed of barley I743, which is a variety of salt stress sensitive barley, were severally subjected to germination. After leaving the seeds at rest for one day, each of the germs was grown in a pot containing a 0.25 mM calcium sulfate solution for two days. Then, the seedlings were further grown for one day in a culture solution (containing 4 mM $KNO_3$, 1 mM $NaNO_3$, 4 mM $NaH_2PO_4$, 2 mM $CaCl_2$, 1 mM $MgSO_4$, 1 ppm Fe, 0.5 ppm B, 0.5 ppm Mn, 0.05 ppm Zn, 0.02 ppm Cu, and 0.01 ppm Mo). Thereafter, sodium chloride was added to the culture fluid so as to make the final concentration 100 mM, and the seedlings were grown therein for additional 12 hours. Then, the roots were harvested and frozen in liquid nitrogen.

(Preparation of Total RNAs and mRNAs Out of the Root of the Salt Stress Tolerant Barley and the Root of the Salt Stress Sensitive Barley)

Preparation of total RNAs and mRNAs out of the root of the salt stress tolerant barley K305 and the root of the salt stress sensitive barley I743 was conducted as follows. Each barley root was frozen and crushed in the liquid nitrogen, and then suspended in a guanidine isothiocyanate solution (containing 4M guanidine isothiocyanate, 25 mM sodium citrate (pH 7.0), 0.5% sodium N-lauryl sarcosinate, and 0.1 M 2-mercaptoethanol) and centrifuged (10,000 rpm, 15 minutes, 20° C.) therein. Each supernatant fluid thus obtained was layered on a cesium chloride solution and further centrifuged (100,000 rpm, 3 hours, 20° C.) therein. Each of the precipitates thus obtained was dissolved in a TES solution (containing 10 mM Tris-HCL (pH 7.4), 5 mM EDTA, and 1% SDS), and extracted by phenol/chloroform extraction. Thereafter, 1/10 quantity of 3M sodium acetate (pH 5.2) and 2.5 quantity of ethanol were added thereto, and the solution was allowed to stand for one night at −20° C. The solutions which were allowed to stand for one night were centrifuged in 15,000 rpm at 4° C. for 20 min, and then the obtained precipitates were severally dissolved into water to form total RNA samples. The total RNA samples were provided to prepare mRNAs thereby in accordance with the attached protocol with "Dynabeads Oligo $(dT)_{25}$" (made by Veritas Corp.).

(Isolation of a Salt Stress Tolerant Barley-Specific cDNA Fragment)

An mRNA, which was equivalent to a difference between the mRNA obtained from the root of the salt stress tolerant barley K305 and the mRNA obtained from the root of the salt stress sensitive barley I743, was collected and used for preparing a salt stress tolerant barley-specific cDNA fragment. Preparation of the salt stress tolerant barley-specific cDNA fragment was conducted as will be described below, while using "PCR-Select cDNA Subtraction Kit" (made by Clontech).

Firstly, cDNAs were synthesized by using the mRNA obtained from the root of the salt stress tolerant barley K305 and the mRNA obtained from the root of the salt stress sensitive barley I743, respectively. Next, the synthesized cDNAs were severally digested with a restriction enzyme RsaI. The obtained cDNA of the salt stress tolerant barley K305 was split into two, and adapters severally having different nucleic sequences were ligated to both ends of the cDNAs. The respective cDNAs after ligation were subjected to hybridization while adding an excessive amount of the cDNA of the salt stress sensitive barley I743. Then, the solutions after hybridization were mixed together and again subjected to hybridization while adding the cDNA of the salt stress sensitive barley I743 which was transformed to a single strand. The hybridization-completed solution thus obtained was then subjected to PCR while using an adapter-specific primer, whereby the cDNA fragment being present only in the root of the salt stress tolerant barley K305 was amplified. The cDNA fragment, which was the PCR product, was then utilized for fabrication of a cDNA fragment library while using "pGEM-T and pGEM-T Easy Vector Systems" (made by Promega Corp.) The cDNA fragment was prepared from this library, and the Northern analysis was conducted with the cDNA fragment as a probe, which was labeled by using "AlkPhos Direct system for chemiluminescence" (made by Amersham Pharmacia Biotech).

The Northern analysis was conducted as follows. Specifically, the total RNAs of the root of the salt stress tolerant barley and the root of the salt stress sensitive barley were prepared according to the above-described method, and the total RNA thus obtained were subjected to electrophoresis by use of a denatured agarose gel (containing 1.2% agarose, 6.3% formaldehyde, 20 mM MOPS, 5 mM sodium acetate, and 1 mM EDTA (pH 7.0)). The RNAs fractionated within the agarose gel were transcribed to nylon membranes and then subjected to hybridization while using the labeled cDNA as the probe.

Such hybridization was conducted as follows. First, the nylon membranes on which the RNAs have been transcribed were blocked with a hybridization buffer. Thereafter, the probe was added onto the hybridization buffer and the nylon membranes were kept at 55° C. for 16 hours. After that, the nylon membranes were subjected to washing processes for two times severally for 10 minutes at 55° C. by use of a washing fluid (containing 2 M urea, 0.1% SDS, 50 mM sodium phosphate (pH 7.0), 150 mM NaCl, 10 mM $MgCl_2$, and 0.2% blocking reagent), and further, subjected to washing processes for two times severally for 5 minutes at a room temperature with the washing fluid. After the washing processes, the nylon membranes were dipped in a CDP-Star solution for 5 minutes at a room temperature. Then, detection of bands bonding the cDNA was performed. FIG. 1 illustrates results of such detection. In FIG. 1, lane 1 shows a result of electrophoresis of the total RNA obtained from the root of the barley K305 which was not subjected to the salt stress treatment, lane 2 shows a result of electrophoresis of the total RNA obtained from the root of the barley K305 which was subjected to the salt stress treatment for 12 hours, lane 3 shows a result of electrophoresis of the total RNA obtained from the root of the barley I743 which was not subjected to the salt stress treatment, and lane 4 shows a result of electrophoresis of the total RNA obtained from the root of the barley I743 which was subjected to the salt stress treatment for 12 hours.

As shown in FIG. 1, the mRNA of the salt stress tolerant barley-specific cDNA fragment (the Sub4 gene) did not exist in the roots of the salt stress sensitive barley I743 but emerged strongly and specifically in the roots of the salt stress tolerant barley K305. Moreover, in the root of the salt stress tolerant barley K305 being exposed to the salt stress for 12 hours, an increase in expression of the mRNA of the Sub4 gene was observed at about double as compared to the same root before exposure to the salt stress. Such an aspect indicated that the cDNA fragment of the salt stress tolerant barley, which was isolated in the above-described processes, emerges and functions specifically in the root of the salt stress tolerant barley K305, and the expression level thereof increased along with the salt stress.

Example 2

(Isolation of a Salt Stress Tolerant Barley-Specific cDNA)

A cDNA library was fabricated from the mRNA obtained from the root of the salt stress tolerant barley K305 by use of "Marathon cDNA Amplification Kit" (made by Clontech) and "pGEM-T and pGEM-T Easy Vector Systems" (made by Promega Corp.). Colony hybridization was performed while using the obtained Sub4 gene fragment as a probe, and then cDNA screening was carried out.

Such hybridization was conducted under the following condition. Specifically, respective colonies in the cDNA library were transcribed to a nylon membrane, and this nylon membrane was blocked by use of a hybridization buffer. A probe was prepared by labeling the Sub4 gene fragment with "AlkPhos Direct system for chemiluminescence" (made by Amersham Pharmacia Biotech), and the nylon membrane finished with blocking was retained at 55° C. for 16 hours together with the probe. Then the nylon membrane was subjected to washing processes for two times severally for 10 minutes at 55° C. by use of the above-described washing fluid, and further, subjected to washing processes for two times severally for 5 minutes at a room temperature with the washing fluid. Thereafter, the nylon membrane was dipped in a CDP-Star solution for 5 minutes at a room temperature. Then, detection of positive colonies bonding the cDNA was performed to isolate the salt stress tolerant barley-specific cDNA.

Example 3

(Determination of a Base Sequence of the Salt Stress Tolerant Barley-Specific cDNA and an Amino Acid Sequence of a Translation Product)

Next, a base sequence of the Sub4 gene being the obtained salt stress tolerant barley-specific cDNA was determined. The base sequence is shown in SEQ. ID. NO. 1 in Sequence Listing. Determination of the base sequence was conducted by use of "BigDye Terminator Cycle Sequencing FS Ready Reaction Kit" (made by Perkin Elmer Inc.) and "Genetic Analyzer ABI PRISM 310" (made by Perkin Elmer Inc.).

An amino acid sequence of a translation product estimated from the base sequence of the Sub4 gene determined herein, which is the salt stress tolerant barley-specific cDNA, is shown in SEQ. ID. NO. 2 in Sequence Listing. Note that the amino acid sequence of SEQ. ID. NO. 2 in Sequence Listing corresponds to the base sequence of SEQ. ID. NO. 1, from the 64th start codon (ATG) to the 1057th stop codon (TGA) thereof.

Example 4

(Homology Search)

Homology comparison was carried out by means of comparing the Sub4 gene being the obtained salt stress tolerant barley-specific cDNA and the amino acid sequence estimated from the base sequence thereof, with known genes and amino acid sequences on a data base. As a result, the obtained gene did not show high homology with other nucleic acids or other amino acids in terms of the nucleic acid level and the amino acid level. Hence the obtained gene and amino acid sequence were proved to be a novel gene and a novel protein, respectively.

Example 5

(Isolation of an Open Leading Frame of the Salt Stress Tolerant Barley-Specific cDNA)

Isolation of an open leading frame of the Sub4 gene was performed by amplification in accordance with the PCR method while setting the cDNA of the Sub4 gene as a template and using a primer including the 64th start codon (ATG) as well as a primer including the 1057th stop codon (TGA). The primers used therein were a primer EXN1/Sub4: gcagctgctg ctcatatgga acaaaat (SEQ. ID. NO. 3 in Sequence Listing) and a primer EXC1/Sub4: ttgaaggcag gatcctcagg aagtcca (SEQ. ID. NO. 4 in Sequence Listing). Note that the primer EXN1/Sub4 is complementary to the sequence of SEQ. ID. NO. 1 from the 49th to 60th positions and from the 64th to 75th positions; meanwhile, the 61st G is substituted by C, the 62nd T is substituted by A, and the 63rd A is substituted by T, respectively. On the contrary, the primer EXC1/Sub4 is complementary to the sequence of SEQ. ID. NO. 1 from the 1048th to 1059th positions and from the 1063rd to 1074th positions; meanwhile, the 1060th A is substituted by G, the 1061st A is substituted by G, and the 1062nd G is substituted by A, respectively.

The PCR reaction was conducted by use of "Advantage 2 PCR Kit" (made by Clontech) and in accordance with the protocol attached thereto. Here, conditions of the PCR reaction were defined as: repeating the routine "at 94° C. for 15 seconds, at 55° C. for 15 seconds, and at 68° C. for 60 seconds" for 30 cycles; and then at 68° C. for 5 minutes. As a result, it was able to isolate an open leading frame region of the Sub4 gene as long as 1028 base pairs. The open leading frame region of the Sub4 gene was sub-cloned to a vector pGEM-T by use of "pGEM-T and pGEM-T Easy Vector Systems" (made by Promega Corp.).

Example 6

(Expression of the Open Leading Frame of the Salt Stress Tolerant Barley-Specific cDNA)

A plasmid was fabricated by means of introducing the isolated open leading frame region of the salt stress tolerant barley-specific gene Sub4 to an *Escherichia coli* expression vector while using "pET Expression System plus Competent Cells" (made by Novagen Inc.), and then induction of expression of the protein was carried out.

Figure 2:
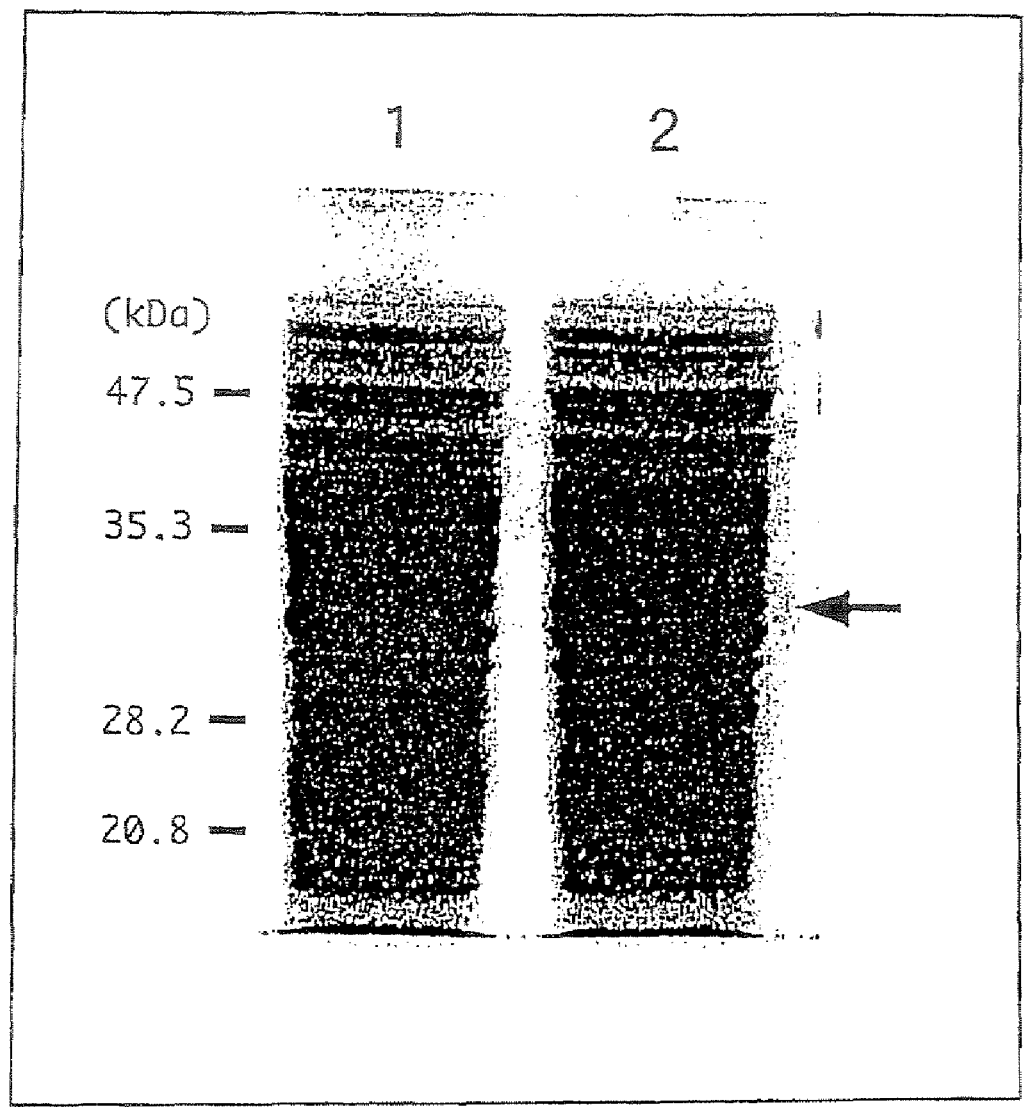
FIG. 2 is an electrophoretic photograph of expression patterns detected by the SDS-PAGE regarding a transcription product of a Sub4 gene showing expression specifically in the salt stress tolerant barley, in the case where the transcription product induce the expression in *Escherichia coli*.

First, the above-described plasmid made by introducing the open leading region of the Sub4 gene to the pGEM-T was digested with restriction enzymes NdeI and BamHI. The DNA fragments digested by the enzymes NdeI and BamHI were inserted to recognition sites with NdeI and BamHI in pET15b, in accordance with "pET System Manual" (made by Novagen Inc.). The plasmid pEXsub4 thus obtained was used for transforming *E. coli* BL21(DE3)pLysS, so as to be subjected to the expression of a transcription product of the open leading frame of the Sub4 gene. Specifically, the transformed *E. coli* was grown in an LB culture medium until 600-nm absorbance reached 0.4. Thereafter, IPTG (to make 1 mM concentration) was added to a culture fluid, and the transformed *E. coli* was further subjected to shaking culture at 37° C. for 8 hours. The culture fluid was then centrifuged, and an obtained *Escherichia coli* bacterial cell was suspended in a sample buffer (containing 50 mM Tris-HCl (pH 6.8), 4% SDS, and 10% glycerol). After boiling for 10 minutes, detection of the protein being manifested the expression was carried out in a 12% SDS-PAGE. FIG. 2 shows the result. In FIG. 2, lane 1 shows an electrophoretic pattern of the *Escherichia coli* bacterial cell subjected to introduction of only the pET15b, and lane 2 shows an electrophoretic pattern of the *Escherichia coli* bacterial cell subjected to introduction of the pEXsub4.

As shown in FIG. 2, a protein band equivalent to a molecular weight of approximately 33,000 was recognized in the *Escherichia coli* showed the expression of the open leading frame of the Sub4 gene. Such a molecular weight was extremely close to the molecular weight at 36,663 of the protein to be calculated from the amino acid sequence of SEQ. ID. NO. 2, thus the expression of the targeted protein in the transformed *Escherichia coli* was confirmed.

Example 7

(Salt Stress Tolerance of the Transformed *Escherichia coli*)

Salt stress tolerance of the transformed *Escherichia coli* fabricated in Example 6 was examined to ascertain as to whether or not the Sub4 gene is directly related to the salt stress tolerance. The *E. coli* BL21(DE3)pLysS (pET15b), which was transformed with the plasmid pET15b that did not contain the Sub4 gene, was used as an object.

Figure 3:
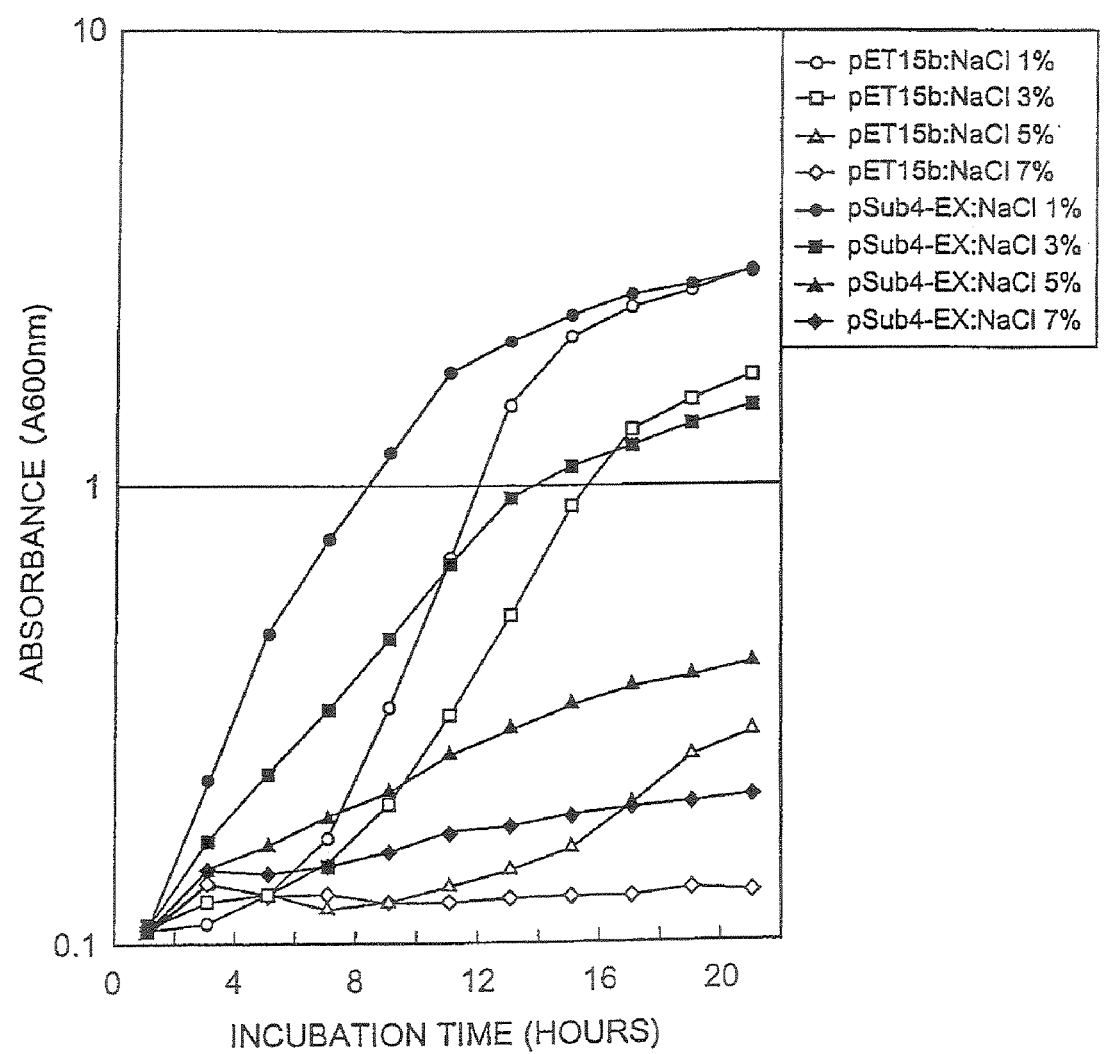
FIG. 3 is a graph showing relations between incubation time and growth rates under various conditions of salt concentrations concerning the genetically transformed *Escherichia coli* including the Sub4 gene showing expression specifically in the salt stress tolerant barley.

The above-described *Escherichia coli* was cultivated in an LB culture medium containing ampicillin (to make 50 µg/ml concentration) and then gathered by centrifugation. The gathered *Escherichia coli* was then suspended in a new LB culture medium containing ampicillin, and subjected to shaking culture by 160 rpm at 25° C. for 1 hour. Subsequently, IPTG (to make 0.5 mM concentration) was added to the fluid after cultivation so as to induce the expression of the introduced gene, and the fluid was again subjected to shaking culture for 1 hour. Absorbance (600 nm) of the fluid was measured, and then the fluid was suspended in the same culture medium containing IPTG and ampicillin until the absorbance (600 nm) reached 0.1. Simultaneously, NaCl was added to the LB culture medium so as to make various concentrations of 1%, 3%, 5%, and 7%. Those samples were subjected to shaking culture at 25° C., and growth rates were measured thereafter. The results are shown in FIG. 3. In the graph, the transformed *Escherichia coli* containing the Sub4 gene was indicated as pSub4-EX, and the *Escherichia coli* transformed only by the pET15b was indicated as pET15b.

As a result, the *E. coli* BL21(DE3)pLysS (pEXsub4) transformed by the plasmid containing the Sub4 gene initiated growth irrespective of the various NaCl concentrations sooner than the object *E. coli* BL21(DE3)pLysS (pET15b), and the growth rates were also faster. Such results indicated that the salt stress tolerance of the *Escherichia coli* was improved by expression of the Sub4 gene in the *Escherichia coli*. Moreover, the results strongly suggested that the Sub4 gene product operated as a molecule having a function to improve salt stress tolerance of a plant.

INDUSTRIAL APPLICABILITY

As described above, the nucleic acid and the protein of the present invention, which are designed to be subjected to the induction of expression under salt stress, are characterized by increasing an expression level under salt stress. Therefore, the present invention is capable of providing the novel protein with a function to impart salt stress tolerance to a plant, and providing the novel gene encoding the protein. Hence, fabrication of a transgenic plant having salt stress tolerance becomes feasible by using the novel gene.

The invention claimed is:
1. An isolated protein comprising SEQ ID NO:2.

* * * * *